United States Patent [19]
Murakami et al.

[11] Patent Number: 6,159,723
[45] Date of Patent: Dec. 12, 2000

[54] RENIN-ACTIVE SUBSTANCE

[75] Inventors: Kazuo Murakami, Tsukuba; Yukio Nakamura; Fumiaki Suzuki, both of Gifu; Yuichi Ishida, 8-205, West Heights, 1947, Oaza Higashiowa, Washimiya-machi, Kitakatsushika-gun, Saitama, all of Japan

[73] Assignees: Tokiwa Chemical Industries, Ltd., Tokyo; Yuichi Ishida, Saitama, both of Japan

[21] Appl. No.: 09/417,305

[22] Filed: Oct. 13, 1999

[30] Foreign Application Priority Data

Oct. 13, 1998 [JP] Japan .................................. 10-291124

[51] Int. Cl.[7] .............................. C12N 9/96; C12N 9/64; C07K 16/00; C12P 21/08
[52] U.S. Cl. ...................... 435/226; 435/188; 530/388.26
[58] Field of Search ........................... 530/389.2, 388.26; 424/178.1; 435/188, 226

[56] References Cited

U.S. PATENT DOCUMENTS 5,763,211  6/1998  Snodgrass et al. .
5,945,512  8/1999  Murakami et al. .

OTHER PUBLICATIONS

F. H. M. Derkx et al., Journal of Biological Chemistry, 267 (32) 22837–42 (Nov. 15, 1992).

Patent Abstracts of Japan, vol. 010, No. 364 (P–524), Dec. 5, 1986, abstract of JP 61 160058 A.

Suzuki et al., Bioscience Biotechnology and Biochemistry, vol. 63, No. 3, pp. 550–554 (Mar. 1999).

Ishizuka et al.–Characterization of MAbS Against Human Prorenir Proeragment & ID of Active Prorenins in Plasma. J Biochem 106:430–435, 1989.

Paul et al.–Fundamental Immunology, 4th Ed. pp. 107 & 657, 1999.

*Primary Examiner*—Christina Y. Chan
*Assistant Examiner*—Gerald R. Ewoldt
*Attorney, Agent, or Firm*—Wenderoth, Lind & Ponack, L.L.P.

[57] ABSTRACT

Disclosed is a novel renin-active substance by utilizing a anti-peptide antibody capable of specifically recognizing a specific amino acid sequence in the human propenin profragment exemplified, as a typical example, by a complex formed from human prorenin and an anti-peptide antibody capable of specifically recognizing an amino acid sequence consisting of at least 15 amino acid residues located within an amino acid sequence consisting of 33 amino acid residues between the isoleucine residue at the 11th site and the arginine residue at the 43rd site within human propenin profragment having an amino acid sequence consisting of 43 amino acid residues.

8 Claims, 5 Drawing Sheets

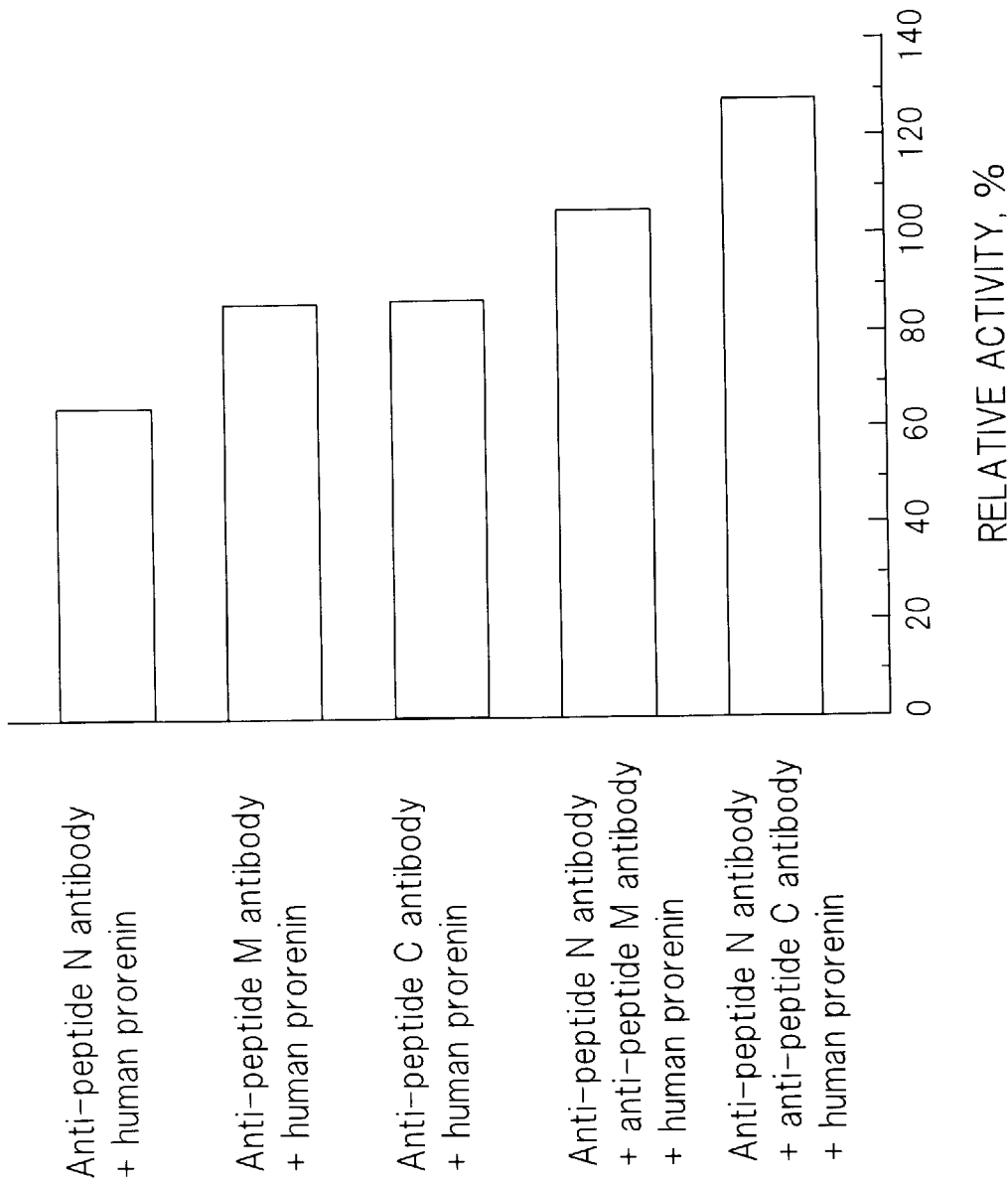

SEQUENCE LISTING

```
<160> NUMBER OF SEQ ID NOS: 4

<210> SEQ ID NO 1
<211> LENGTH: 43
<212> TYPE: PRT
<213> ORGANISM: Artificial Sequence
<220> FEATURE:
<223> OTHER INFORMATION: Description of Artificial Sequence: peptide

<400> SEQUENCE: 1

Leu Pro Thr Asp Thr Thr Thr Phe Lys Arg Ile Phe Leu Lys Arg Met
 1               5                  10                  15

Pro Ser Ile Arg Glu Ser Leu Lys Glu Arg Gly Val Asp Met Ala Arg
                20                  25                  30

Leu Gly Pro Glu Trp Ser Gln Pro Met Lys Arg
            35                  40

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: peptide

<400> SEQUENCE: 2

Ile Phe Leu Lys Arg Met Pro Ser Ile Arg Glu Ser Leu Lys Glu Arg
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: peptide

<400> SEQUENCE: 3

Gly Val Asp Met Ala Arg Leu Gly Pro Glu Trp Ser Gln Pro Met
 1               5                  10                  15
```

```
-continued

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 4

Leu Pro Thr Asp Thr Thr Thr Phe Lys Arg Ile
 1               5                  10
```

RENIN-ACTIVE SUBSTANCE

BACKGROUND OF THE INVENTION

The present invention relates to a novel renin-active substance which exhibits enzymatic activity or, namely, renin activity as a combination of the human prorenin with an anti-peptide-specific antibody capable of forming an immunocomplex by combining with the profragment peptide of human prorenin.

Prorenin is produced mainly in the kidney as a precursor of the completely matured renin or, namely, as the completely matured renin having a profragment with a sequence of 43 amino acid residues combined at the N-terminal thereof and released into blood.

While the concentration of this prorenin in blood is about 10 times higher than the completely matured renin, the prorenin per se does not exhibit any enzymatic activity so that it is a conventional practice to convert the same into the completely matured renin by decoupling the profragment portion with a protease such as trypsin and pepsin.

Non-enzymatic methods were also proposed some years ago. For example, a method is proposed for activation at a low temperature in an acidic condition without alteration in the primary structure in Nature, volume 288, pages 702–705 (1980), Journal of Biological Chemistry, volume 262, pages 2472–2477 (1987), Clinical Chemistry, volume 37, pages 1811–1819 (1991), Journal of Biological Chemistry, volume 267, pages 11753–11759 (1992) and elsewhere. Furthermore, Journal of Biological Chemistry, volume 267, pages 22837–22842 (1992) teaches a method in which a low-molecular renin inhibitor is brought into combination with the renin-active portion of the prorenin buried in the deep groove of the three-dimensional structure to convert the same into the open type so that an antibody capable of recognizing the vicinity of the active portion of the completely matured renin is enabled to combine.

Although many reports are available on the subject matter of formation of an immunocomplex when the anti-intermediate-portion and anti-C-terminal peptide antibodies of the prorenin profragment are bound with prorenin, none of the reports are suggestive of the enzymatic activity exhibited thereby.

SUMMARY OF THE INVENTION

The present invention accordingly has an object to provide a novel renin-active substance by utilizing an anti-peptide antibody capable of recognizing a specific amino acid sequence within the human prorenin profragment.

The inventors were successful in providing a renin-active substance which is a complex of the human prorenin and an antibody capable of specifically recognizing, as an antigen, a peptide having an amino acid sequence at the N-terminal portion of the prorenin profragment or, namely, consisting of 15 amino acid residues between the leucine residue at the 1st site and the arginine residue at the 15th site.

As a result of further continued investigations, the inventors have been led to completion of the present invention on the base of several unexpected discoveries. Firstly, a renin-active substance is obtained by combining the human prorenin with an antibody capable of specifically recognizing a peptide having an amino acid sequence involved within the amino acid sequence consisting of the 33 amino acid residues of the human prorenin profragment between the isoleucine residue at the 11th site and the arginine residue at the 43rd site. Secondly, an improvement in the renin activity can be accomplished by a complex of the human prorenin and a mixed antibody consisting of the above mentioned antibody and equivalent or equimolar amounts of a second anti-peptide antibody capable of specifically recognizing an amino acid sequence consisting of the 11 amino acid residues in the human prorenin profragment between the leucine residue at the 1st site and the isoleucine residue at the 11th site as compared with the combination of the human prorenin and each of the respective single anti-peptide antibodies.

Thus, the present invention provides, according to a first aspect of the invention, a complex of the human prorenin and an anti-peptide antibody capable of specifically recognizing an amino acid sequence consisting of at least 15 amino acid residues within an amino acid sequence consisting of the 33 amino acid residues between the isoleucine residue at the 11th site and the arginine residue at the 43rd site within human prorenin profragment having an amino acid sequence consisting of 43 amino acid residues.

The present invention further provides, according to a second aspect of the invention, a renin-active substance which is a complex of the human prorenin and a mixed antibody consisting of equimolar amounts of a first anti-peptide antibody capable of specifically recognizing an amino acid sequence consisting of at least 15 amino acid residues within an amino acid sequence consisting of the 33 amino acid residues between the isoleucine residue at the 11th site and the arginine residue at the 43rd site within the human prorenin profragment having an amino acid sequence consisting of 43 amino acid residues and a second anti-peptide antibody capable of specifically recognizing an amino acid sequence consisting of 11 amino acid residues within the above mentioned human prorenin profragment between the leucine residue at the 1st site and the isoleucine residue at the 11th site.

BRIEF DESCRIPTION OF THE DRAWING

FIG. 5 is a bar chart showing relative degrees of activation in complexes of human prorenin with various anti-peptide antibodies.

DETAILED DESCRIPTION OF THE PREFERRED EMBODIMENTS

Figure 1:
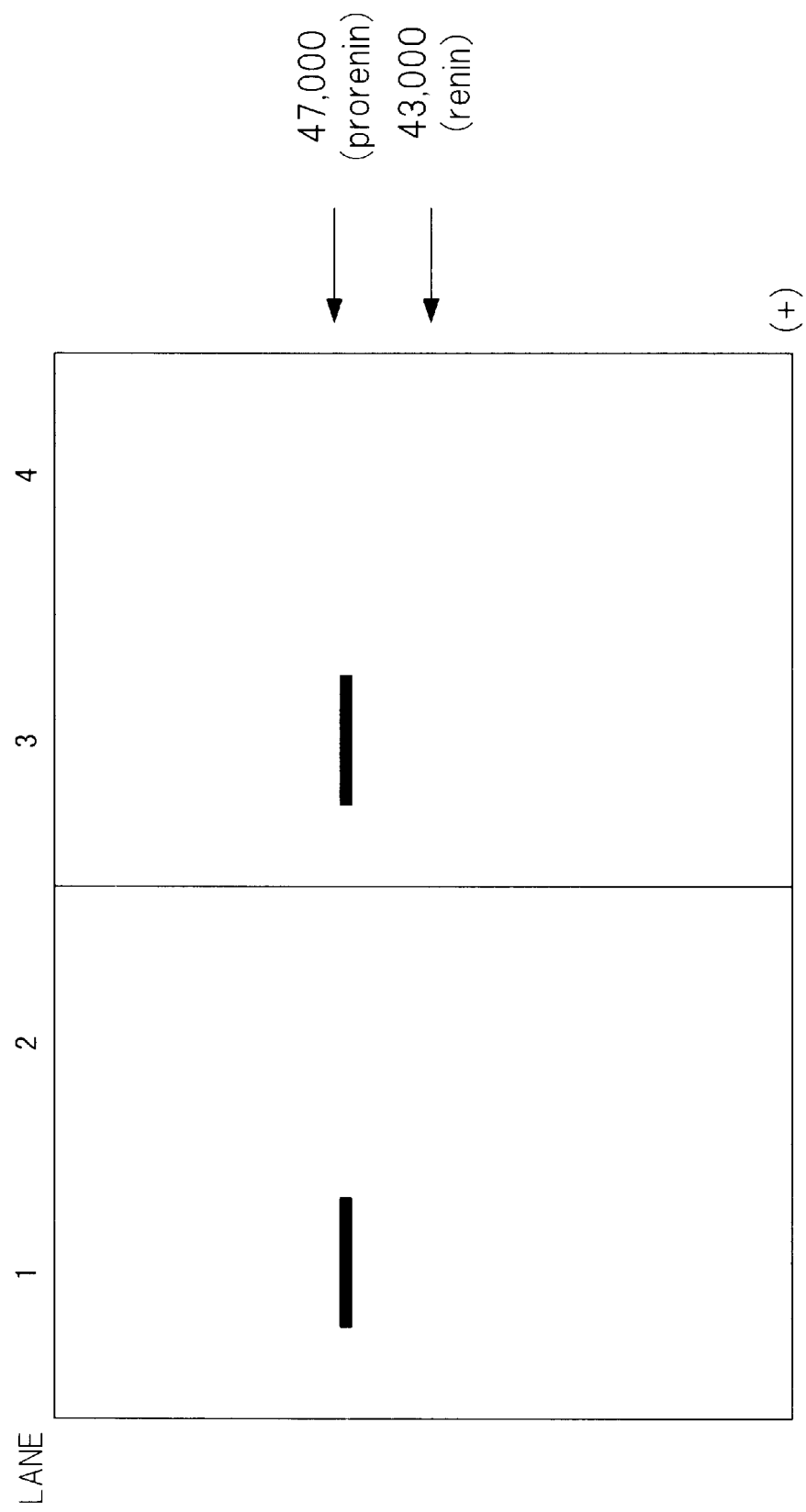
FIG. 1 is a diagram showing the results of the Western blot analysis of the human prorenin and completely matured renin.

The present invention provides a renin-active substance which is a complex between an anti-peptide antibody and human prorenin characterized by the specificity of the anti-peptide antibody that the anti-peptide antibody specifically recognizes a peptide having an amino acid sequence consisting of at least 15 amino acid residues at any positions within the amino acid sequence consisting of 33 amino acid residues within the human prorenin profragment between the isoleucine residue at the 11th site and the arginine residue at the 43rd site.

Greatly enhanced renin activity can be obtained by using a mixed antibody consisting of equimolar amounts of the above mentioned anti-peptide antibody and a second anti-peptide antibody capable of specifically recognizing an amino acid sequence consisting of 11 amino acid residues in the above mentioned human prorenin profragment between the leucine residue at the 1st site and the isoleucine residue at the 11th site.

This human prorenin profragment is a substance having an amino acid sequence indicated by the Sequence No. 1 shown below and listed in the SEQUENCE LISTING given later.

```
                                          Sequence No. 1
Leu Pro Thr Asp Thr Thr Phe Lys Arg Ile Phe Leu
 1               5                  10

Lys Arg Met Pro Ser Ile Arg Glu Ser Leu Lys Glu Arg
        15              20                  25

Gly Val Asp Met Ala Arg Leu Gly Pro Glu Trp Ser Gln
            30                  35

Pro Met Lys Arg
    40
```

The renin-active substance of the present invention can be prepared by synthesizing a first peptide, referred to as the peptide M hereinafter, consisting of 16 amino acid residues in the intermediate portion of the prorenin profragment, namely, between the isoleucine residue at the 11th site and the arginine residue at the 26th site and a second peptide, referred to as the peptide C hereinafter, consisting of 15 amino acid residues at the C-terminal portion thereof, namely, between the glycine residue at the 27th site and the methionine residue at the 41st site, both peptides with addition of a Cys residue at the C-terminal thereof and using these peptides according to the method described below.

Thus, these peptides are respectively employed in the preparation of immunogenic antigens by combining with a carrier protein such as bovine serum albumin, ovalbumin, keyhole lympet hemocyanin and the like by using a crosslinking agent such as a maleimide compound. Thereafter, the respective immunogenic antigens admixed with the Freund's perfect adjuvant are subcutaneously administered to a matured rabbit repeatedly at two week intervals to effect immunization. After the fifth administration, a small volume of blood is taken from the ear-peripheral vein to examine the antibody value followed by exsanguination when the antibody value has fully increased to obtain an antiserum. Nextly, the antiserum is subjected to a salting-out treatment and a purification treatment by the affinity chromatography using affinity gels combining the respective synthetic peptides.

The procedure from preparation of the immunogenic antigen to the affinity chromatographic purification of the antibodies can be performed according to a known method described, for example, by S Ohumi, et al. in "Experimental Protocol in Antipeptide Antibodies" (1994), page 48.

In the next place, the anti-peptide antibody after the affinity chromatographic purification is added to a solution of human prorenin diluted with a physiological saline solution containing bovine serum to effect the reaction at a temperature of 4° C. for 16 to 24 hours so as to obtain a complex.

This reaction mixture is then admixed with a sheep angiotensinogen solution as a human renin substrate and incubated at 37° C. for 60 minutes to effect the reaction followed by termination of the reaction by chilling in an ice bath so that angiotensin I is produced in the reaction mixture. Accordingly, this complex is a substance capable of exhibiting enzymatic activity or, namely, renin activity.

Specific binding of the purified antibody and the human prorenin can be confirmed by subjecting the renin-active substance obtained in this manner to the Western blot method and the protein-protein interaction measurement by utilizing surface plasmon resonance.

In the next place, each of the complexes is reacted with sheep angiotensinogen as the renin substrate and comparison of the renin activity is made with the trypsin-treated prorenin as a positive control and with normal rabbit serum as a negative control in place of the antibody.

The results of these comparative tests are that, while the antibody complex exhibits renin activity equivalent to that of the positive control, almost no renin activity is exhibited by the negative control so that it is concluded that this substance is a renin-active substance which is completely different from any known acidity- and low temperature-activated substances as well as from any open substances by a low-molecular renin inhibitor.

FIG. 1 of the accompanying drawing is a diagram showing the results of the Western blot analysis undertaken with human prorenin and a completely matured renin after a trypsin treatment of prorenin having apparent molecular weights of 47,000 and 43,000, respectively, as indicated by the arrows at the right hand, as the reference samples. As is shown in this diagram, spots are found in the lanes 1 and 3 for the prorenin indicating complexing with the anti-peptide C and M antibodies (see below), respectively, at the positions of migration corresponding to a molecular weight of 47,000 while no spots are found in the lanes 2 and 4 for the completely matured renin with the anti-peptide C and M antibodies, respectively.

Figure 2:
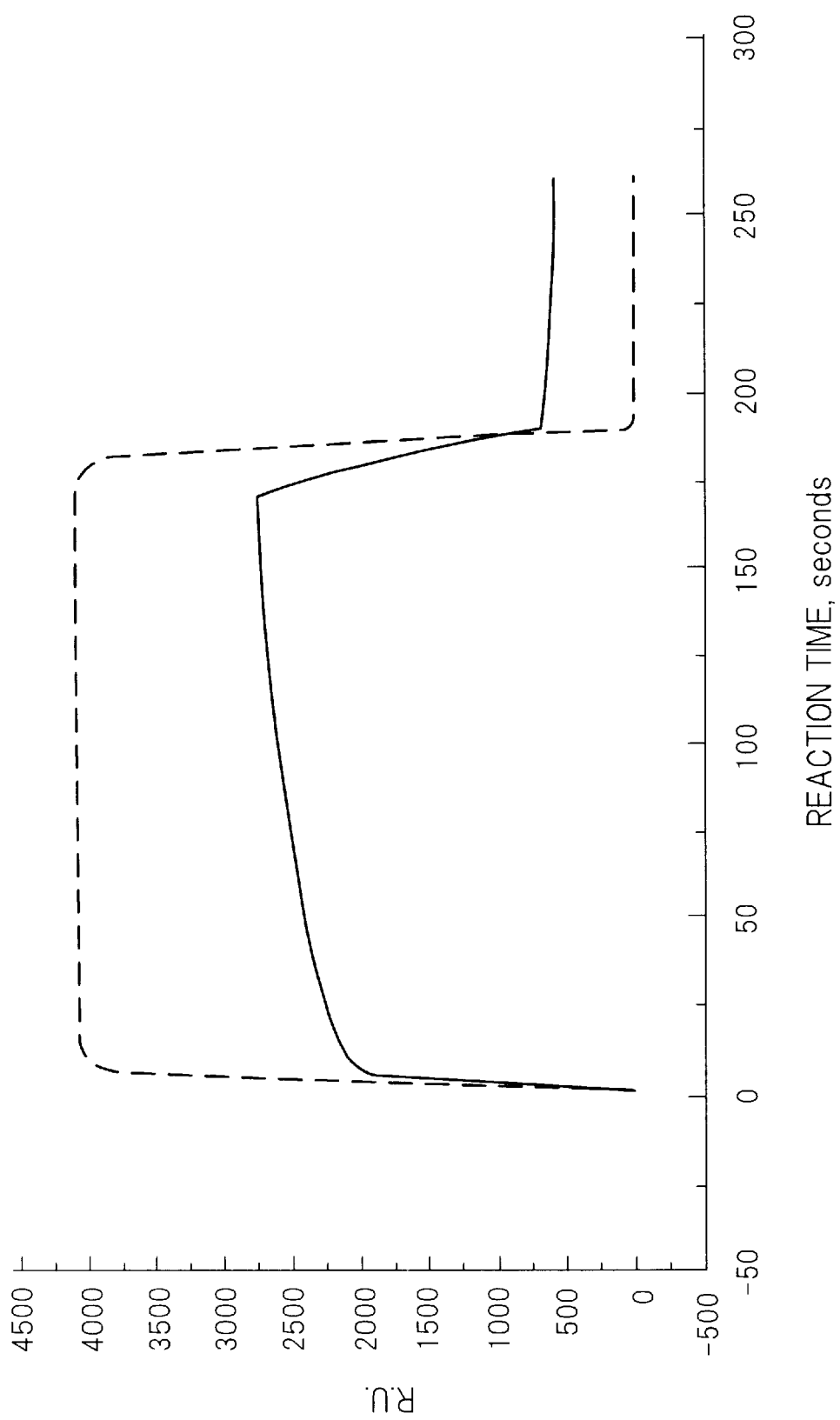
FIG. 2 is a graph showing the binding ability of the anti-peptide antibody at the profragment intermediate portion with prorenin as a function of the reaction time.
Figure 3:
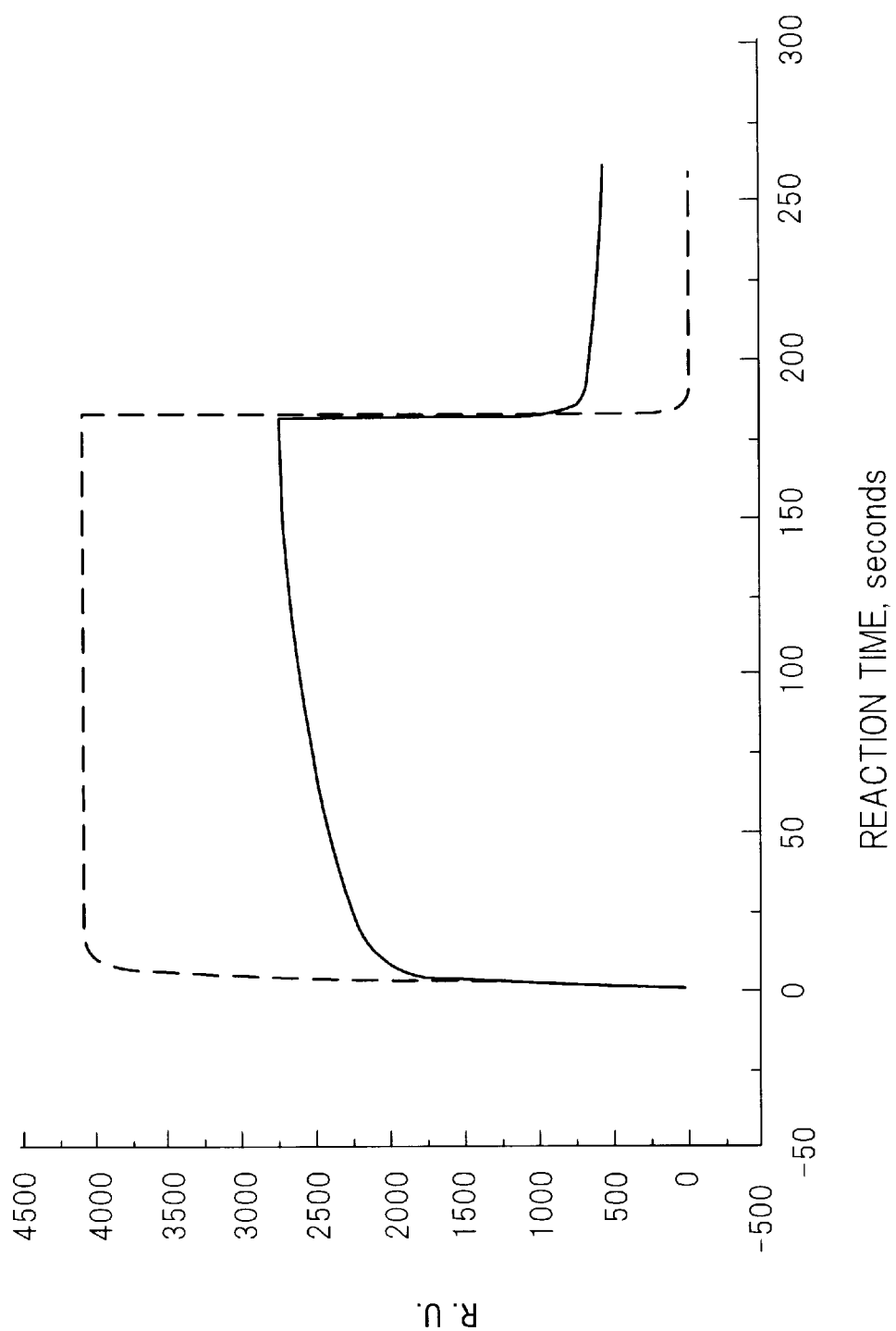
FIG. 3 is a graph showing the binding ability of the anti-peptide antibody at the profragment C-terminal portion with prorenin as a function of the reaction time.

FIGS. 2 and 3 are each a graph showing the results of the plasmon resonance analysis in resonance units (R.U.) at varied reaction times as a measure of the binding ability between the anti-peptide antibody and prorenin determined by the measurement of the changes in the surface plasmon resonance using a protein-protein interaction measuring instrument (Model BIA Core 100, manufactured by Pharmacia Biotech Co.) in which human prorenin was passed at a constant flow rate through a flow cell by chemical binding of the antibody after affinity chromatographic purification. FIG. 2 is for the anti-peptide antibody, referred to as the anti-peptide M antibody hereinafter, capable of specifically recognizing the amino acid sequence consisting of 16 amino acid residues in the prorenin profragment between the isoleucine residue at the 11th site and the arginine residue at the 26th site. FIG. 3 is for the anti-peptide antibody, referred to as the anti-peptide C antibody hereinafter, capable of specifically recognizing the amino acid sequence consisting of 15 amino acid residues in the profragment between the glycine residue at the 27th site and the methionine residue at the 41st site. The solid-line curve and the broken-line curve in each of these figures are for the prorenin and for the control buffer solution, respectively.

As is understood from these figures, while binding with prorenin can be noted for each of the anti-peptide antibodies, binding cannot be noted for the control buffer solution.

Figure 4:
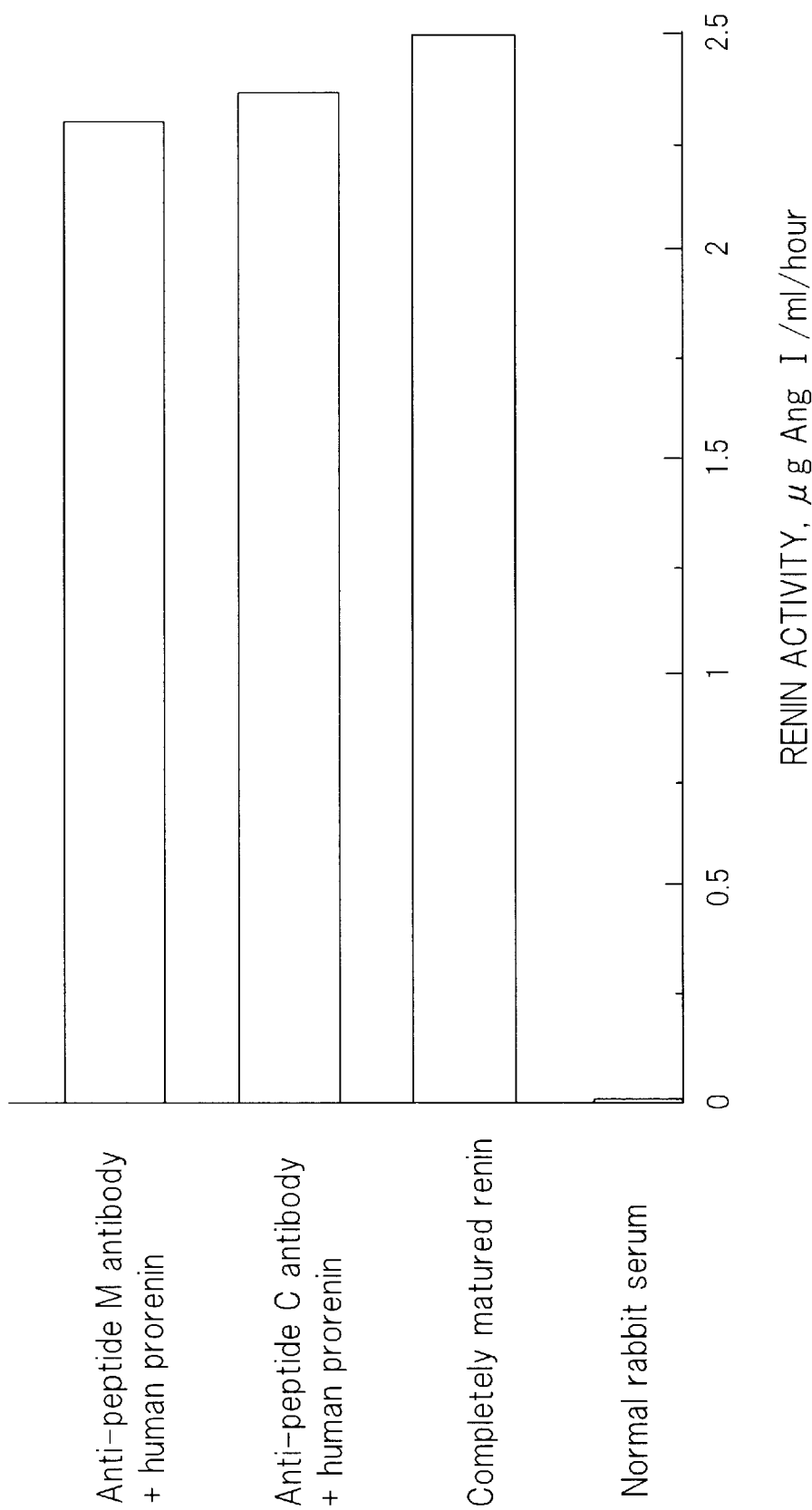
FIG. 4 is a bar chart showing the renin activity of the complexes of anti-peptide antibodies and human prorenin.

FIG. 4 is a bar chart indicating the renin activity determined by the enzymatic immunoassay of the angiotensin I produced by the enzyme or, namely, the renin-active substance when sheep angiotensinogen as a renin substrate is added to and reacted with a complex obtained by the reaction of human prorenin with an anti-peptide antibody after affinity chromatographic purification. As is understood from this figure, while the activity level is about equivalent between the renin activity of the completely matured renin by the trypsin treatment of prorenin as a positive control and the renin activity of the complex between the anti-peptide M antibody or anti-peptide C antibody, almost no renin activity is exhibited in the system by the use of normal rabbit serum in place of the anti-peptide antibody as the negative control.

A conclusion derived therefrom is that the anti-peptide M antibody having an amino acid sequence at the intermediate portion of the prorenin profragment between the 11th site and the 26th site and the anti-peptide C antibody at the C-terminal portion thereof having an amino acid sequence between the 27th site and the 41st site are each capable of binding specifically with human prorenin and the thus formed complexes each exhibit the renin activity so that they are each converted to a renin-active substance which is quite different from any heretofore known activated materials.

FIG. 5 is a bar chart indicating relative renin activities of the complexes including the complex formed by binding, with the human prorenin, of a mixed antibody as an equimolar mixture of the anti-peptide M antibody or anti-peptide C antibody and another anti-peptide antibody, referred to as the anti-peptide N antibody hereinafter, which specifically recognizes an amino acid sequence consisting of eleven amino acid residues in the human prorenin profragment between the leucine residue at the 1st site and the isoleucine residue at the 11th site and the complexes formed by binding of the respective anti-peptide antibodies singly with the human prorenin taking the trypsin activation level of the prorenin employed as 100%. This figure indicates that the renin activity is increased by 1.22 times with a mixture of the anti-peptide M antibody and the anti-peptide N antibody as compared with the anti-peptide M antibody alone and by 1.52 times with a mixture of the anti-peptide C antibody and the anti-peptide N antibody as compared with the anti-peptide C antibody alone. In particular, the renin activity for the combination of the anti-peptide C antibody and the anti-peptide N antibody reaches as high as 128% of the heretofore known activity in the trypsin activation of the prorenin.

In the following, the present invention is described in more detail by way of Examples.

EXAMPLE 1

(1) Preparation of Prorenin Profragment Peptide Immunogenic Antigen

According to the solid-phase method conventionally practiced in the peptide synthesis, a peptide consisting of 17 amino acid residues and having an amino acid sequence of the Sequence No. 2 shown below and listed in the SEQUENCE LISTING with addition of a Cys residue at the C-terminal was synthesized and the reaction mixture was subjected to isolation and purification by the high-performance liquid chromatography.

```
                                         Sequence No. 2
Ile Phe Leu Lys Arg Met Pro Ser Ile Arg Glu Ser Leu
1               5                   10
Lys Glu Arg
    15
```

Separately, a 16 mg portion of hemocyanin as a carrier protein was dissolved in 1 ml of a 0.1 M phosphate buffer solution of pH 7.2 and the solution was admixed with 100 μl of a 15 mg/ml solution of N-(γ-maleimidobutyroxy) succimide in dimethyl formamide to effect the reaction at room temperature for 3 hours. This reaction mixture was subjected to gel filtration by passing the reaction mixture through a Sephadex G-25 column having an inner diameter of 15 mm and length of 300 mm (a product by Pharmacia Bio Co.) to remove unreacted N-(γ-maleimidobutyroxy) succimide followed by elution of the reaction product by using a 0.1 M phosphate buffer solution of pH 6.0 as the eluant.

In the next place, the thus obtained eluate solution was admixed with 10 mg of the purified peptide mentioned above and reaction was effected at room temperature for 3 hours to obtain a peptide hemocyanin complex as an immunogenic antigen. The thus obtained immunogenic antigen of the profragment peptide at the intermediate portion was stored at −80° C. until use.

(2) Preparation of Anti-peptide Antibody

The immunogenic antigen of the profragment peptide obtained in the procedure (1) described above was dissolved in physiological saline solution to have a concentration adjusted to 1 mg protein/ml and the solution was thoroughly mixed with an equivalent amount of the Freund's perfect adjuvant. The mixed solution was subcutaneously injected in portions to several positions of a rabbit of New Zealand white strain having a body weight of about 2.5 kg.

Thereafter, the subcutaneous injection treatment of the rabbit with the immunogenic antigen was repeated at two-week intervals each time with a dose decreased to one-half of that in the first time injection until establishment of a fully enhanced antibody value followed by exsanguination to prepare an antiserum.

(3) Preparation of Purified Antibody by Affinity Chromatography

An affinity chromatographic column of 3 ml volume was prepared by chemically binding a 1 mg portion of the purified peptide obtained in (1) described above to 3 ml of an amine-bonded gel (Affigel 102, a product by Biorad Co.) by using N-(γ-maleimidobutyroxy) succimide.

In the next place, a 10 ml portion of the antiserum obtained in (2) above was mixed with a 0.1 M phosphate buffer solution of pH 7.0 and the mixture was subjected to fractional precipitation by using a 50% ammonium sulfate solution to collect the fraction of IgG. This fraction was solubilized by adding 10 ml of the 0.1 M phosphate buffer solution and subjected to dialysis for 15 hours at 4° C. by using 2000 ml of the same buffer solution.

The whole volume of the IgG solution after dialysis was passed through the above mentioned affinity chromatographic column of 2 ml volume to be completely freed from unadsorbed fractions and the adsorbed antibody was dissolved out with a 0.1 M glycine hydrochloride solution of pH 2.5 immediately followed by neutralization with a 1 M tris buffer solution.

The thus obtained anti-peptide M antibody was stored in a frozen state until fractionation for use.

(4) Preparation of Renin-active Substance

According to a known method described in Journal of Hypertensions, volume 4, pages 388–390 (1986), the cDNA of prorenin originating in human kidney was introduced into an expression vector and built into ovarian cells of a Chinese hamster, referred to as CHO cells hereinafter, followed by culturing in an Eagle's culture medium of the modified Dulbecco method containing 10% of a bovine embryonic serum followed, after full growth of the CHO cells, by replacement with a serum-free culture medium to obtain a cultured supernatant containing recombinant human prorenin.

The thus obtained CHO-cultured supernatant was subjected to dialytic purification with a phosphate-buffered physiological saline solution containing 5 mM of EDTA.

In the next place, an about 8 ng portion of this human prorenin was subjected to electrophoresis according to a conventional procedure on an SDS-polyacrylamide gel in a gel concentration of 7.5% followed by transcription thereof onto a nitrocellulose film to effect reacting and binding with the affinity-purified antibody of the peptide at the intermediate portion of the profragment obtained in (3) described above.

This reaction product was analyzed by color development using an ABC kit (a product by Vector Laboratory Co.) to accomplish confirmation that the antibody was bound at the transfer position of the human prorenin.

Separately, a 8 nM solution of the human prorenin dissolved in a phosphate buffer solution was passed at a flow rate of 10 µl/minute through a flow cell (a product by Pharmacia Biotech Co.) after amine coupling of the affinity-chromatographically purified antibody obtained in (3) above and the changes in the surface plasmon resonance were observed by using a protein-protein interaction measuring instrument to examine the binding condition between the human prorenin and the affinity-chromatographically purified antibody leading to a conclusion that a complex was formed therebetween.

EXAMPLE 2

According to the solid-phase method conventionally practiced in peptide synthesis, a peptide consisting of 16 amino acid residues and having an amino acid sequence of the Sequence No. 3 shown below and listed in the SEQUENCE LISTING with addition of a Cys residue at the C-terminal was synthesized and a peptide-hemocyanin complex, which served as an immunogenic antigen, was prepared therefrom in the same manner as in Example 1.

```
                                          Sequence No. 3
Gly Val Asp Met Ala Arg Leu Gly Pro Glu Trp Ser Gln
  1               5                  10
Pro Met
    15
```

In the next place, an antiserum was prepared from this immunogenic antigen in the same manner as in Example 1 followed by a treatment with an affinity chromatographic column prepared by using the purified peptide to obtain a purified anti-peptide C antibody.

The thus obtained purified antibody was reacted with the human prorenin obtained in the same manner as in Example 1 to prepare a renin-active substance.

EXAMPLE 3

According to the solid-phase method conventionally practiced in peptide synthesis, a peptide consisting of 12 amino acid residues and having an amino acid sequence of the Sequence No. 4 shown below and listed in the SEQUENCE LISTING with addition of a Cys residue at the C-terminal was synthesized and a peptide-hemocyanin complex to serve as an immunogenic antigen was prepared therefrom in the same manner as in Example 1.

```
                                       Sequence No. 4
Leu Pro Thr Asp Thr Thr Thr Phe Lys Arg Ile
  1           5                    10
```

In the next place, an antiserum was prepared from this immunogenic antigen in the same manner as in Example 1 followed by a treatment with an affinity chromatographic column prepared by using the purified peptide to obtain a purified anti-peptide N antibody.

A 50 µl portion of a 0.6 µM human prorenin solution was admixed with 50 µl of a 0.6 µM solution of the purified anti-peptide M antibody obtained in Example 1 or the purified anti-peptide C antibody obtained in Example 2 and 50 µl of a 0.6 µM solution of the purified anti-peptide N antibody obtained in the above described manner and the reaction therebetween was effected at 4° C. for 20 hours to prepare a renin-active substances by the reaction of the respective mixed antibodies with human prorenin. Reference Example 1.

(1) Preparation of Enzyme-labeled Angiotensin I

A 5 mg portion of horseradish peroxidase (a product by Behringer Manheim Co.) was dissolved in a 0.2 M phosphate buffer solution and the solution was admixed with 1 ml of a 2.5% aqueous solution of glutaraldehyde to effect the reaction followed by gel filtration to remove unreacted glutaraldehyde.

Thereafter, this solution was admixed with 130 µl of an aqueous solution prepared by dissolving 1 mg of synthetic angiotensin I (a product by Peptide Laboratories) in 1 ml of purified water to effect the reaction followed by addition of a 0.2 M aqueous solution of lysine to terminate the reaction. The unreacted angiotensin I was removed from the solution by undertaking another gel filtration treatment to give 1.5 ml of a solution of the enzyme-labeled angiotensin I.

(2) Preparation of Antiangiotensin I Antibody

A 3.6 mg portion of the synthetic angiotensin I was dissolved in a 0.2 M phosphate buffer solution and to this solution was added dropwise a solution prepared by dissolving 3.6 mg of N-(γ-maleimidobutyroxy) succimide in tetrahydrofuran to effect the reaction at 30° C. for 30 minutes followed by the addition of ethyl alcohol and diethyl ether and standing at −80° C. for 10 minutes to precipitate a crystalline matter, which was washed twice with diethyl ether to give a composite of the angiotensin I and N-(γ-maleimidobutyroxy) succimide.

Separately, a 10 mg portion of bovine serum albumin was dissolved in 2 ml of a 0.2 M tris hydrochloride buffer solution of pH 8.6 containing 8 M of urea and the solution was admixed with 15 µmoles of dithiothreitol (a product by Sigma Co.) to effect the reaction at 37° C. for 1 hour followed by addition of 3 ml of a 10% trichloroacetic acid solution to precipitate a solid matter which was washed three times with distilled water to give a reduced bovine serum albumin.

In the next place, the composite of the angiotensin I and N-(γ-maleimidobutyroxy) succimide and the reduced bovine serum albumin were jointly dissolved in 1.5 ml of a 0.2 M aqueous solution of EDTA-Na containing 6 M of urea to effect the reaction at 25° C. for 2 hours. After completion of the reaction, the reaction mixture was subjected to dialysis to give a complex of the angiotensin I and bovine serum albumin as an immunogenic antigen. This solution was stored at −80° C. until use for immunization of test animals.

(3) Antiangiotensin I Antibody

An antiserum was prepared by the treatment of the complex of the angiotensin I and bovine serum albumin as the immunogenic antigen in the same manner as in Example 2.

(4) Antiangiotensin I Antibody Plate

The above mentioned antiangiotensin I antibody was diluted by 5000 times with a 0.05 M sodium hydrogencarbonate solution of pH 9.6 and a 100 µl portion of the solution was put into each well of a 96-well microplate (a product by Gleiner Co.) and kept standing at 4° C. for 16 hours to be immobilized on the microplate. A 200 μl portion of a phosphate buffer solution containing 1% of bovine serum albumin was then added to each well of the microplate bearing the immobilized antiangiotensin I antibody.

(5) Renin Activity of Complexes

A 50 μl portion of a 0.6 nM human prorenin solution was admixed with 50 μl of a 0.6 μM solution of the affinity-chromatographically purified anti-peptide M or C antibody and the reaction was effected at 4° C. for 20 hours to form a complex. The reaction mixture was admixed with 100 μl of an angiotensinogen reagent to effect the reaction at 37° C. for 60 minutes followed by termination of the reaction by transfer of the mixture onto an ice bath.

Thereafter, the mixture was further admixed with 100 μl of the above described solution of the enzyme-labeled angiotensin I and a 100 μl portion of the mixture was transferred onto each well of the above mentioned antiangiotensin I antibody plate which was gently whirled at 25° C. for 2 hours.

Further, a 200 μl portion of a chromogenic reagent was added to each well to develop a color by the reaction at 25° C. for 15 minutes and the reaction was terminated by the addition of 100 μl of a 1 N phosphoric acid solution. The light absorbance was determined at a wavelength of 450 nm by using a calorimeter.

As a positive control, the same procedure as described above was undertaken by using 100 μl of the completely matured renin. Further, as a negative control, the same procedure as described above was undertaken by replacing the anti-peptide M or C antibody added to the human prorenin solution with the same amount of a normal rabbit serum.

It was found as a result of the control tests that, while the renin activity was exhibited when the human prorenin formed a complex with the anti-peptide M or C antibody, the strength of the renin activity being substantially at the same level as that of the completely matured renin as the positive control, almost no renin activity was exhibited by the human prorenin as the negative control.

These results supported the conclusion that the human prorenin was converted into a complex capable of exhibiting the renin activity when bound with the anti-peptide M or C antibody.

What is claimed is:

1. A renin-active substance which is a complex formed from human prorenin and a mixture of a first anti-peptide antibody capable of specifically recognizing a first amino acid sequence between an isoleucine residue at the 11th site and an arginine residue at the 43rd site within human prorenin profragment as shown in Sequence No. 1 and a second anti-peptide antibody capable of specifically recognizing a second amino acid sequence between a leucine residue at the 1st site and an isoleucine residue at the 11th site in the human prorenin profragment.

2. A renin-active substance which is a complex formed from human prorenin and an anti-peptide antibody capable of specifically recognizing an amino acid sequence in human prorenin profragment as shown in Sequence No. 1 between a glycine residue at the 27th site and a methionine residue at the 41st site.

3. A renin-active substance which is a complex formed from human prorenin and a mixture of a first anti-peptide antibody capable of specifically recognizing a first amino acid sequence in human prorenin profragment as shown in Sequence No. 1 between an isoleucine residue at the 11th site and an arginine residue at the 26th site and a second anti-peptide antibody capable of specifically recognizing a second amino acid sequence in the human prorenin profragment between a leucine residue at the 1st site and an isoleucine residue at the 11th site.

4. A renin-active substance which is a complex formed from human prorenin and a mixture of a first anti-peptide antibody capable of specifically recognizing a first amino acid sequence in human prorenin profragment as shown in Sequence No. 1 between a glycine residue at the 27th site and a methionine residue at the 41st site and a second anti-peptide antibody capable of specifically recognizing a second amino acid sequence in the human prorenin profragment between a leucine residue at the 1st site and an isoleucine residue at the 11th site.

5. The renin-active substance according to claim 1 wherein the first amino acid sequence is shown in Sequence No. 3.

6. The renin-active substance according to claim 2 wherein the amino acid sequence is shown in Sequence No. 3.

7. The renin-active substance according to claim 3 wherein the first amino acid sequence is shown in Sequence No. 2.

8. The renin-active substance according to claim 4 wherein the first amino acid sequence is shown in Sequence No. 3.

* * * * *